United States Patent [19]

Svensson

[11] Patent Number: 4,524,474
[45] Date of Patent: Jun. 25, 1985

[54] ABSORPTION PAD

[75] Inventor: Sven A. T. Svensson, Halmstad, Sweden

[73] Assignee: Duni Bila AB, Sweden

[21] Appl. No.: 488,742

[22] Filed: Apr. 26, 1983

[30] Foreign Application Priority Data

Apr. 29, 1982 [SE] Sweden ............................. 8202716

[51] Int. Cl.³ ........................... A47G 9/02; A61G 9/00
[52] U.S. Cl. ........................................... 5/484; 5/487; 604/381
[58] Field of Search ................... 5/484, 487, 482, 502, 5/500; 604/380, 381, 378, 379

[56] References Cited

U.S. PATENT DOCUMENTS 2,707,289 5/1955 Taggart .................................. 5/484
4,045,833 9/1977 Mesek et al. ........................... 5/484

FOREIGN PATENT DOCUMENTS 1107411 8/1981 Canada .................................. 5/484
2501848 8/1975 Fed. Rep. of Germany .......... 5/484
2080351 2/1982 United Kingdom .................... 5/484

Primary Examiner—Alexander Grosz
Attorney, Agent, or Firm—Ostrolenk, Faber, Gerb & Soffen

[57] ABSTRACT

An absorption pad useful for protecting a bed, furniture, or the like, includes a lower liquid impervious material layer and an upper liquid absorbent material layer laminated thereto. The liquid absorbent layer is impregnated with strings or filaments of a liquid resistant agent which does not stiffen the pad. The strings or filaments form a grid-like pattern for defining compartments between the strings over preferably the entire area of the absorption pad, thereby for limiting the spread of liquid over the pad. The layers are laminated together, and may be laminated by an adhesive. The laminating areas may be in a filament pattern corresponding to and overlapping the filament pattern of the strings of the liquid resistant agent.

9 Claims, 4 Drawing Figures

ABSORPTION PAD

BACKGROUND OF THE INVENTION

The present invention relates to an absorption pad for protecting objects, like beds and furniture against liquid excretions. The pad includes a layer of liquid impervious material and a layer of liquid-absorbent material attached thereto.

With so-called bed protectors presently available for protecting beds and the like, and particularly with such protectors used in medical care, the liquid excreted by a patient lies on and spreads outward to the edges of the bed protector. If the excretion is of large volume, the liquid often runs out over the edges of the protector where it wets any undersheet and the mattress beneath.

SUMMARY OF THE INVENTION

The present invention provides an absorption pad, e.g. in the form of the aforementioned bed protector, which eliminates the above described disadvantages. The distinguishing feature of the invention is that the liquid-absorbent material layer is impregnated with a liquid-resistant agent, having a geometric design on the pad and a composition such that it does not have a disadvantageous stiffening effect. That agent is disposed in an array of strings or filaments to form a pattern of catchment compartments, which are preferably arrayed over the entire area of the absorption pad. These compartments limit the spread of excreted liquid over the absorption pad.

The invention thereby provides a bed protector, or the like, formed as an absorption pad. With the aid of its liquid-blocking arrangement, the pad prevents liquid excreted on the pad from running beyond the edges, while a favorable spread of the liquid takes place over the whole area of the liquid-absorbing material layer. Any sheet and mattress, or the like beneath the pad, thus remains dry even for large liquid excretions.

Providing lattice-pattern laminating of the absorbent material layer to the liquid impervious layer provides greater absorption, inter alia, since free liquid can be kept between the bottommost fibers in the asborption material and the liquid-impervious material. At the same time, this provides a softer and more pliable combined material with less consumption of adhesive, as compared with laminating using adhesive over the entire mating surfaces. The laminate produced by adhesion in a lattice filament pattern also performs a blocking function in respect of liquid which tends to migrate along the liquid impervious material layer, as compared with a spot-adhered or line-adhered laminate.

The invention is now described in detail with reference to the accompanying drawings showing embodiments of the invention.

DESCRIPTION OF THE PREFERRED EMBODIMENTS

Figure 1:
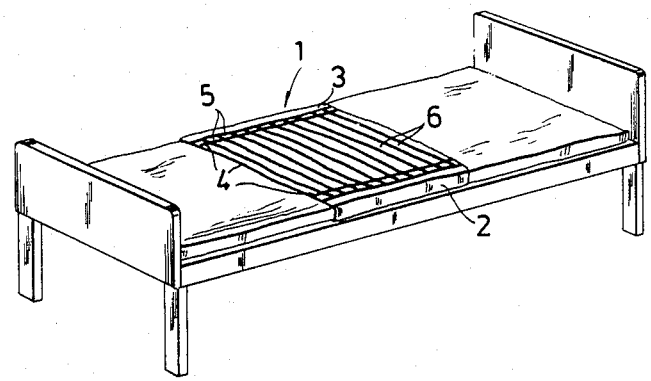
FIG. 1 is a perspective view of a bed having a bed protector in the form of an absorption pad in accordance with the invention, including side flaps tucked under the long sides of the mattress.
Figure 2:
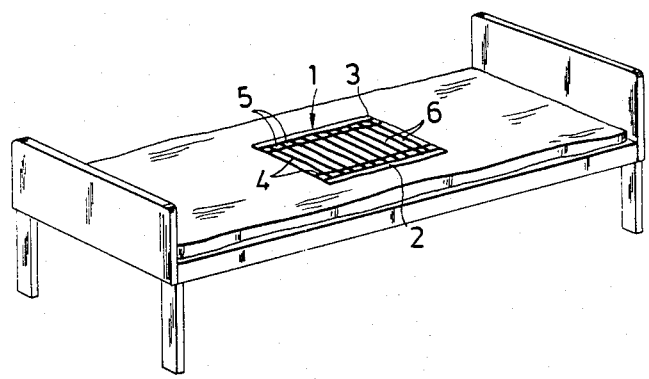
FIG. 2 is the same type of view as FIG. 1, but with another embodiment of the invention lying loosely on a bed.
Figure 3:
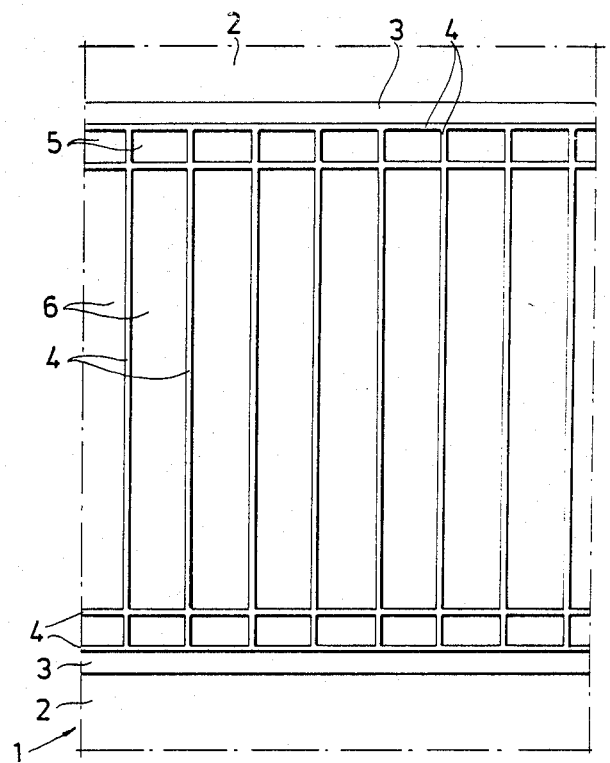
FIG. 3 is a plan view of an embodiment of an absorption pad formed as a bed protector in accordance with the present invention.
Figure 4:
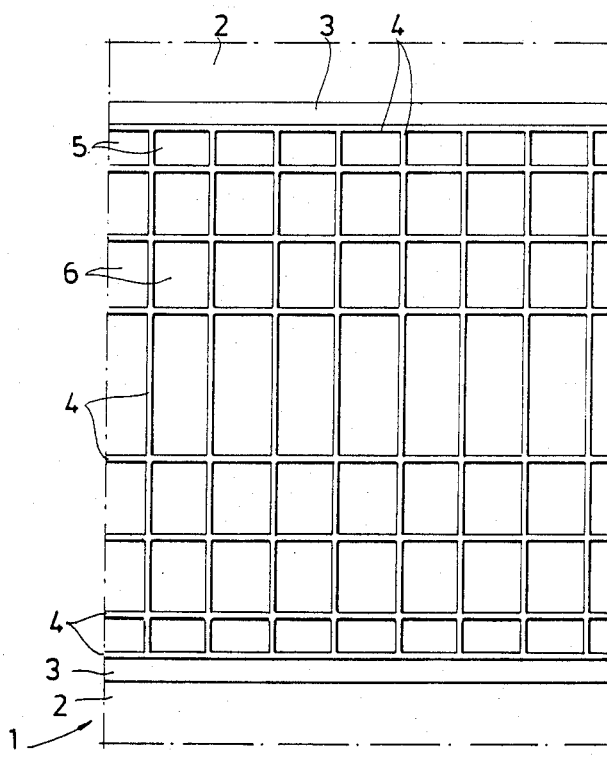
FIG. 4 is a plan view of another embodiment of a bed protector.

The various absorption pads 1 for all of the embodiments illustrated in FIGS. 1-4 includes a liquid-impervious material layer 2, which serves as the under layer of the pad. To the impervious layer is adhered a liquid-absorbent material top layer 3. In FIG. 1, the layer 2 is illustrated as extending laterally past the lateral edges of the layer 3 for enabling the layer 2 to be tucked in under a mattress.

The liquid-absorbent material layer has impregnated in it strings or filaments 4 of the liquid-resistant agent, such as a suitable liquid resistant, impervious, plastic or resin. The resistant agent is of such material and the strings thereof are of such width and thickness that the strings are without any stiffening effect. The strings are arrayed in a grid-like pattern extending, as seen in the longitudinal direction of a bed on which the pad is placed, both transversely and longitudinally over the surface of the asborption material layer 3 to form longitudinally elongate compartments 5 and transversely elongate compartments 6. This pattern causes the liquid to spread in the compartments by first leaving one compartment and entering an adjacent one when the absorption capacity limit of the absorption layer in the first of the compartments has been exceeded. This is also applicable locally along a compartment edge in the areas pressed down by the patient.

The quantity of liquid a compartment may contain or absorb is dependent on the thickness or height of the inter-compartment blocking string 4 and upon the capacity of the liquid-absorbent material layer 3. In the illustrated embodiments in FIGS. 1-4, the height or thickness of the strings has been selected to be about 1 mm, and the width of the strings 4 has been selected to be about 10 mm. In the compartments 5, which are generally rectangular and are located near the lateral edges of the pad, the liquid will be distributed in the longitudinal direction of the compartments 5 after reaching the longer edge strings and before it spills beyond the edges of the compartment. The compartments 5 preferably also can be formed as longitudinal compartments i.e. in the longitudinal direction of the mattress. If the patient gets attention soon after excreting, small compartments extending transversely of the width of the bed are to be preferred. They minimize the risk of wetting the top sheet beneath the bed. The patient thus only needs to lie a short while on the central wetted area. If the patient does not get attention until some time after excreting, long central compartments across the bed are to be preferred so that the liquid spreads outward as much as possible without spilling outside the pad.

The two layers 2 and 3 are preferably laminated together using a lattice-pattern adhesion technique. Less adhesive will accordingly be used than with lamination over the entire mating surfaces. There is also the advantage that a greater amount of liquid can be retained in the absorption pad between the absorbent material layer 3 and the liquid-impervious layer 2. Furthermore, an effective liquid-blocking function is obtained with lattice-pattern adhesion, if the adhesive filaments in the lamination lattice pattern have a dimension relationship to the width of the string 4, which prevents liquid migration under the string 4. The liquid-absorbent material layer 3 may also be laminated to the liquid-impervious layer 2 over the whole of minor portions of the mating surfaces in register with the pattern of the strings 4, i.e. in identical coacting patterns. This is the preferred arrangement of the laminating adhesive, and since the adhesive and the strings are coextensive, no additional showing of the adhesive has been made in the drawings. The bottoms of the compartments can then be laminated in a larger lattice pattern of adhesive filaments than that required under the strings 4. By a suitable relationship between the sizes of these two lattices, an effective liquid barrier is obtained at the interface between the two layers 2 and 3.

Impregnating the liquid-absorbent material 3 from both sides before lamination has the advantage that the blocking function will also be ensured at the surface engaging against the liquid-impervious layer 2. As mentioned above, the pattern of strings 4 can be varied in relation to the coacting properties of the absorption material layer 3 and the liquid resistant agent in respect of the excreted liquid.

In some fields of use, such as incontinence, bedwetting, accidents, surgery, home nursing, baby care, etc., when the inventive absorption pad is used as a protector for beds, seats, pillows, operation cushions, etc., it may be suitable to arrange the inventive absorption pad with compartments 5 and 6 confined or constituted by impregnated strings 4.

Although the present invention has been described in connection with the preferred embodiments thereof, many variations and modifications will now become apparent to those skilled in the art. It is preferred, therefore, that the present invention be limited not by the specific disclosure herein, but only by the appended claims.

What is claimed is:

1. An absorption pad for protecting a bed, furniture, or the like, the pad comprising:

a liquid impervious material layer, a liquid absorbent layer affixed over the impervious layer;

a liquid resistant agent impregnated into the absorbent material layer; the impregnated agent being arrayed over the absorbent material layer in a plurality of strings of the agent for defining a pattern of compartments separated by the strings for limiting the spread of liquid over the pad the layers being laminated together in such a manner that liquid migration under the strings is prevented, whereby after a compartment is saturated with liquid, the liquid overflows over the strings into adjacent compartments.

2. The absorption pad of claim 1, wherein the strings are arrayed to define the compartments over the entire area of the pad.

3. The absorption pad of claim 1, wherein the strings of liquid resistant agent extend both transversely and longitudinally of the pad to form the compartments.

4. The absorption pad of claim 3, wherein the strings of agent are placed to define transversely elongate compartments and to define longitudinally elongate compartments.

5. The absorption pad of claim 4, wherein the longitudinally elongate compartments are disposed to define rows of the longitudinally elongate compartments parallel to the lateral edges of the pad.

6. The absorption pad of claim 5, wherein there is a respective row of longitudinally elongate compartments disposed at each of the opposite lateral edges of the pad.

7. The absorption pad of claim 1, wherein the lamination of the layers is with an adhesive.

8. The absorption pad of claim 1, wherein the lamination together uses a filament pattern.

9. The absorption pad of claim 8, wherein the lamination together is with an adhesive.

* * * * *